(12) United States Patent
Russell et al.

(10) Patent No.: US 7,034,939 B2
(45) Date of Patent: Apr. 25, 2006

(54) CALIBRATION SYSTEM AND METHOD FOR CALIBRATION OF VARIOUS TYPES OF POLARIMETERS

(75) Inventors: Edgar Russell, Goleta, CA (US); Brian Cairns, New York, NY (US)

(73) Assignee: SpecTIR Corporation, Santa Barbara, CA (US)

( * ) Notice: Subject to any disclaimer, the term of this patent is extended or adjusted under 35 U.S.C. 154(b) by 301 days.

(21) Appl. No.: 10/385,171

(22) Filed: Mar. 11, 2003

(65) Prior Publication Data

US 2003/0174328 A1 Sep. 18, 2003

Related U.S. Application Data

(60) Provisional application No. 60/363,308, filed on Mar. 11, 2002.

(51) Int. Cl.
*G01J 4/00* (2006.01)

(52) U.S. Cl. .................................. 356/366; 356/367

(58) Field of Classification Search ................ 356/364, 356/366, 367

See application file for complete search history.

(56) References Cited

U.S. PATENT DOCUMENTS

| | | | |
|---|---|---|---|
| 4,118,125 A | 10/1978 | Gundermann | |
| 4,306,809 A | 12/1981 | Azzam | |
| 5,149,959 A | 9/1992 | Collins et al. | |
| 6,043,887 A | 3/2000 | Allard et al. | |
| 6,052,187 A * | 4/2000 | Krishnan et al. | 356/364 |
| 6,177,995 B1 | 1/2001 | Compain et al. | |
| 6,490,043 B1 | 12/2002 | Kebabian | |
| 6,804,003 B1 * | 10/2004 | Wang et al. | 356/369 |

OTHER PUBLICATIONS

Azzam, R. M. A., "Multichannel polarization state detectors for time-resolved ellipsometry," Elsevier Sequoia 1993, pp. 371-374.

* cited by examiner

*Primary Examiner*—Gregory J. Toatley, Jr.
*Assistant Examiner*—Roy M. Punnoose
(74) *Attorney, Agent, or Firm*—Dickstein Shapiro Morin & Oshinsky LLP

(57) ABSTRACT

A calibration system is integrally provided with a polarimeter in which the calibration system and the polarimeter each receives a radiance sample. Radiances provided by the calibration system used to provide the relative responsivity calibrations among the polarimeter channels are essentially depolarized so as to provide the measurement data required to update the relative responsivity factors for the polarimeter channels. The unpolarized radiances from the calibrator are interspersed with scene data collected directly by the polarimeter, so that the polarimeter can effectively be recalibrated for each set of scene data obtained by the polarimeter. Another part of the calibration system may be used to adjust the scaling of the polarization calculated from the scene data obtained by the polarimeter. This is achieved by providing radiances which are essentially 100% polarized.

42 Claims, 6 Drawing Sheets

CALIBRATION SYSTEM AND METHOD FOR CALIBRATION OF VARIOUS TYPES OF POLARIMETERS

This application claims priority to U.S. Provisional Application Ser. No. 60/363,308, filed Mar. 11, 2002, which is hereby incorporated by reference in its entirety.

FIELD OF THE INVENTION

This invention relates to an apparatus and method of calibrating a polarimeter used for sensing scene signals from which the polarization of the scene can be derived.

BACKGROUND OF THE INVENTION

Polarimetry has long been used in many industrial and research-oriented applications such as organic chemistry, biology, pharmacology, and astronomy. More recently, polarimetry has proven to be highly valuable in a wide range of imaging applications using the measured intensities (radiances) and polarization of scenes. For example, polarimetric measurements can be used to obtain accurate and detailed characterizations for applications such as mineralogic mapping, urban growth monitoring, pollution assessment, and vegetation and environmental analysis, to name a few.

Unlike the traditional applications of polarimetry, in which the sampling and analysis are performed with the instrumentation and the research subject arranged in substantially stationary relationship relative to each other, more extensive polarimetric measurements often requires the scene information to be gathered from a moving platform, such as may be achieved by mounting and operating a polarimeter on an aircraft. The polarimeter is thus exposed to environmental conditions, such as temperature, pressure, humidity, contamination, etc., which may vary frequently during the data gathering operation. In order to obtain data which is consistently reliable in such applications, it is desirable to be able calibrate the polarimeter whenever changes in operating conditions occur, rather than only performing the calibrations in a laboratory setting preceding and/or following deployment into the field.

BRIEF SUMMARY OF THE INVENTION

The present invention enables a polarimeter that will typically perform measurements at multiple wavelengths to obtain consistently accurate scene data regardless of changing environmental and operating conditions while collecting calibration data interposed with measurement data collected from the scene. In particular, the present invention includes a calibrator for calibrating a polarimeter, an operationally integrated system including the calibrator and a polarimeter, and also a method of calibrating a polarimeter.

A scene is polarimetrically measured by performing a plurality of linear scans across the scene, wherein during each linear scan across the scene, the polarimeter collects a plurality of radiance samples of the scene. In the invention, a calibrator is located approximately along the peripheral region(s) of the angular swath of each scan cycle at which radiance samples are viewed by the polarimeter. The calibrator receives radiance samples from the scene and then depolarizes them through a scrambler. The polarimeter views the scene both directly and via the calibrator during each scan cycle. Each radiance sample viewed through the calibrator is essentially depolarized which allows determination of the relative responsivity factors among the sensor channels of the polarimeter used in the determination of the scene polarization. Typically, multiple spectral bands will be measured by a polarimeter. This calibration data is acquired interspersed with scene data collected directly by the polarimeter, so that the polarimeter can effectively be recalibrated as frequently as warranted by changes in conditions. Such tracking of the calibration data can be studied for trends to assess instrument stability and to assess the appropriate means to preserve the measurement accuracy over periods where such changes occur.

The calibrator of the present invention may also be used to adjust the scaling of the polarization ultimately calculated from the scene data obtained by the polarimeter. To perform this function, the calibrator obtains a radiance sample taken from the scene and produces a sample that is essentially 100% linearly polarized. Comparing the degree of polarization measured viewing the calibrator versus the known polarization produced by the calibrator allows determination of any required non-unity scaling factor to be applied to the scene polarization measurements.

The operationally integrated calibrator and polarimeter system of the present invention may include a selector which continuously scans the scene to deliver a line of radiance samples to the polarimeter including a) one or more substantially depolarized radiance samples from a first portion of the calibrator for calibrating the polarimeter, b) one or more (usually many) radiance samples directly viewed by the polarimeter, c) one or more 100% polarized radiance samples from the second portion of the calibrator for modifying scaling factors for the measured polarization values, and d) a dark reference zone for collecting "dark signal" samples in the polarimeter for setting the zero-radiance levels of the signal channels.

BRIEF DESCRIPTION OF THE DRAWINGS

The foregoing and other advantages and features of the invention will become more apparent from the detailed description of exemplary embodiments of the invention given below with reference to the accompanying drawings in which.

DETAILED DESCRIPTION OF THE INVENTION

Figure 1A:
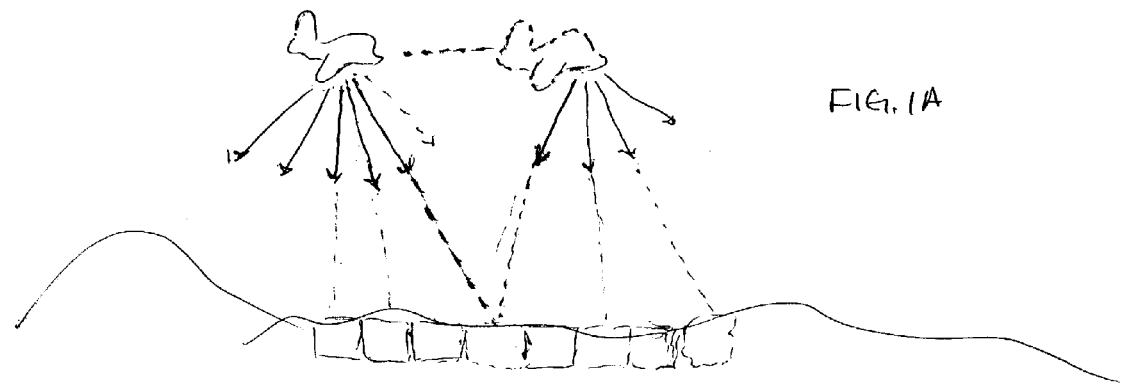
FIG. 1A illustrates a first method of obtaining scene radiance samples in connection with the present invention.
Figure 1B:
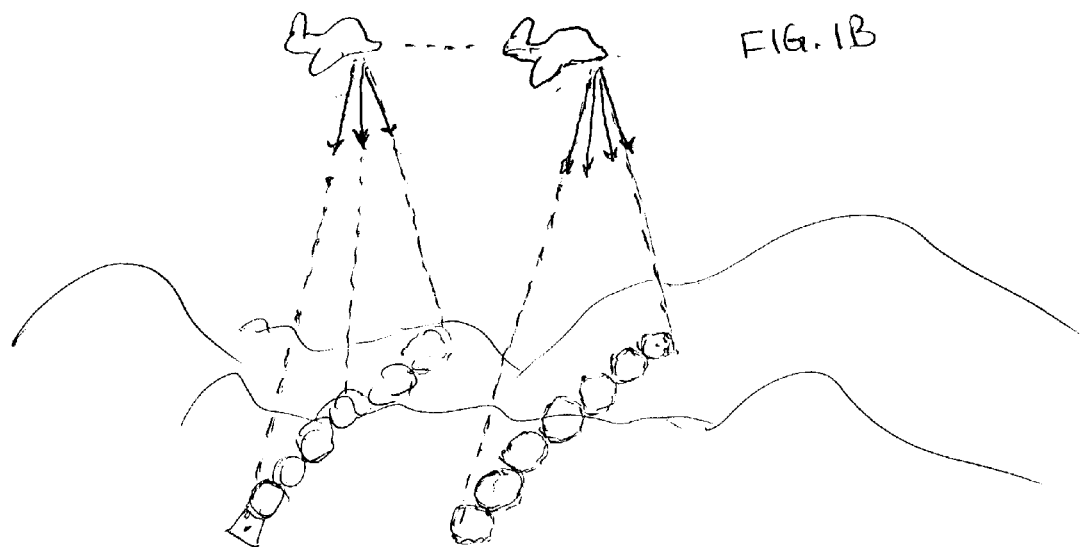
FIG. 1B illustrates a second method of obtaining scene radiance samples in connection with the present invention.

The present invention may be used during the acquisition of scene data by a polarimeter located on a moving platform, such as on an airplane. The visual field encompassing the entire scene to be sampled is continuously scanned in a series of linear sweeps across the scene performed with a rotating scanner, so that each linear sweep results in a new "line" of the scene being scanned by the scanner rotating through an angular swath. Scanning along the direction of motion is termed along-track scanning which provides multi-angle views of scene elements located along the ground track, as illustrated in FIG. 1A. Alternatively, scene data may be acquired during scanning with the scan plane oriented perpendicular to the direction of motion, known as cross-track scanning. This is illustrated in FIG. 1B where the angular range of the scene views is diminished, but polarization "images" can be created by reconstruction of measurement data collected in this fashion As the scene is being scanned, the polarimeter obtains a number of radiance samples, e.g., at every 0.8°, from the scene within each angular swath of the visual field.

Radiance samples obtained by the sensor channels of a polarimeter are processed in a manner that can be described by a Mueller matrix for each signal channel. Knowledge of the Mueller matrix—essentially the calibration factors—allows determination of intensity and polarization of scene samples to be determined which can be alternately described by the Stokes vector representation, i.e., (I, Q, U, V), for each scene sample. The Stokes vector notation provides a convenient representation for the intensity and polarization properties of a scene, although the Stokes components I, Q, U, and V vary with wavelength, illumination and viewing geometry, etc. An advantage of organizing the measured scene data from the polarimeter in a Stokes vector representation is that there are a number of calculation simplifications that result when the appropriate Mueller matrices are combined using matrix multiplication. The Mueller matrices used in the polarimeter represent the parameters of the polarimeter and various optical transformations, e.g., reflection or scatter, affecting the intensity and polarization levels of the radiance samples obtained from the scene. The resultant overall system Mueller matrix when applied to the original Stokes vector of the raw scene data yields the Stokes vector representation of the output.

Another way to represent the scene is by relating the intensity and polarization according to the relationship $$P=[(Q/I)^2+(U/I)^2+(V/I)^2]^{0.5}, \tag{1}$$

and the angles $\alpha$ and $\gamma$, wherein I is intensity and P is polarization. Q, U, and V are the same components used in the Stokes vector, wherein Q and U represent linearly polarized components of the scene radiance, and V represents circular polarization of light. $\alpha$ represents the angular azimuth of the linear polarization components of the scene, and $\gamma$ represents the angle of the circular polarization component. In most situations where the scattering of sunlight is being measured, the fourth Stokes component V is negligible compared to the intensity and linear polarization components. In such cases, greater instrumental simplicity of a polarimeter may be achieved by measuring only linear polarization, so that when measured with a polarimeter measuring only linear polarization, any circular component would not be distinguishable from the unpolarized term. Although the present invention is described below as a system and method for calibrating a polarimeter designed for measuring only linear polarization, the invention is also applicable to polarimeters which sense the fourth Stokes component, i.e., that measure the circular polarization component of the viewed scene.

The polarimeter used in connection with the present invention preferably provides a pair of optical assemblies such as a pair of bore-sighted telescopes, each having two or more sensor channels to measure the polarization components of the viewed scene. However, polarimeters having only one sensor channel per optical assembly may also be used. The telescopes are arranged so that any quantitative difference in the radiance samples obtained from the scene between the paired telescopes is negligible relative to the range of the entire scene being measured. Nevertheless, the present invention is capable of accounting for any differences in the samples viewed between the paired telescopes. Even if only a single sensor channel is used to obtain radiance samples from the scene, the calibrator and method are still useful for tracking the polarization response of the channel. In a particular demonstration of the invention, the polarimeter used in conjunction with the operationally integrated calibrator includes three sets of paired, parallel sensor channels forming a total of six bore-sighted telescopes with each telescope pair servicing three spectral bands.

From the equation representing the polarization of the scene radiance given above, it is seen that polarization P is a ratiometric quantity, unlike intensity I, for which the absolute magnitude is often of major importance. Each sensor channel measures the intensity of a radiance sample at a different azimuth polarization in a spectral band than that measured by the other sensor channels for that specific spectral band. In the interest of simplicity and clarity, the invention will be explained below with reference to an example which includes one pair of bore-sighted telescopes having four sensor channels (arranged two each per telescope) each sensing in the same spectral band, although in practical applications of the invention, the polarimeter may provide many more than four sensor channels and service multiple spectral bands.

In the explanatory embodiment, one pair of sensor channels in the first of two bore-sighted telescopes may measure the linearly polarized scene intensities denoted by $I(\theta_{11})$ and $I(\theta_{12})$, while another pair of sensor channels in the second bore-sighted telescope may measure the linearly polarized scene intensities denoted by $I(\theta_{21})$ and $I(\theta_{22})$ in a spectral band, wherein $\theta_{11}$, $\theta_{12}$, $\theta_{21}$, and $\theta_{22}$ indicate the azimuth of the linearly polarized component measured. To provide a representative range across the spectral band, it may be preferred to select the azimuth positions measured by sensor channels so that one pair of channels perform measurements at orthogonal azimuths, and the other pair perform measurements at azumuths which are rotated 45° from the first pair. For example, suitable values for $\theta_{11}$, $\theta_{12}$, $\theta_{21}$, and $\theta_{22}$ in this embodiment include $\theta_{11}=0$, $\theta_{12}=90$, $\theta_{21}=45$ and $\theta_{22}=135$. If the signal values measured for each of the polarized scene intensities are represented by $S(\theta_{11})$ and $S(\theta_{12})$ and by $S(\theta_{21})$ and $S(\theta_{22})$, respectively, then the signal values are related to the polarized intensities by $$I(\theta_{11})=k*S(\theta_{11}), \tag{2}$$

$$I(\theta_{12})=k*K1*S(\theta_{12}), \tag{3}$$

$$I(\theta_{21})=k*C12*S(\theta_{21}) \tag{4}$$

and $$I(\theta_{22})=k*C12*K2*S(\theta_{22}), \tag{5}$$

where k, K1, K2 and C12 are constants for an ideally functioning polarimeter. Specifically, k represents the scaling factor between the measured value for the detected intensity (radiance) level measured by the signal channel and the actual value of the polarized scene radiance viewed, while K1 represents the intra-telescope relative responsivity factor between the channels measuring orthogonal positions, e.g., $I(\theta_{11})$ and $I(\theta_{12})$ in the first telescope. Similarly, K2 represents the intra-telescope relative responsivity factor between the channels measuring orthogonal polarizations, e.g., $I(\theta_{21})$ and $I(\theta_{22})$ in the second telescope of the paired set, and C12 is an intensity (radiance) responsivity factor that adjusts the measurements of the second telescope of the pair so as to yield the same value as that from the first telescope.

In order to obtain consistently accurate polarimetric data, it is essential that the polarization calibrator enable the accurate determination of the K1 and K2 factors for each calibration sample taken. Specifically, the intra-telescope relative responsivity factors K1 and K2 must be known to a high degree of accuracy, typically to better than 0.1% uncertainty, to achieve and maintain the desired polarimetric accuracy.

The determination of K1 and K2 requires that the radiance viewed by each telescope is essentially unpolarized, so that the intensity value measured in each sensor channel is the same for all polarization azimuths in the spectral band. This is achieved by positioning a psuedodepolarizer or polarization scrambler in the polarization calibrator, as will be described further below. In this example, for unpolarized light, $$I(\theta_{11})=I(\theta_{12}), \tag{6}$$

and $$I(\theta_{21})=I(\theta_{22}), \tag{7}$$

so that $$k*S(\theta_{11})=k*K1*S(\theta_{12}), \tag{8}$$

and $$k*C12*S(\theta_{21})=k*C12*K2*S(\theta_{22}). \tag{9}$$

Since the constant factors k and C12 cancel out, K1 and K2 can be calculated respectively, by $$K1=S(\theta_{11})/S(\theta_{12}), \tag{10}$$

and $$K2=S(\theta_{21})/S(\theta_{22}). \tag{11}$$

It is important to note that it is not necessary that the radiance levels of the samples viewed by the two telescopes be identical, i.e., that $I(\theta_{11})+I(\theta_{12})=I(\theta_{21})+I(\theta_{22})$, for the determination of the K1 and K2 factors, since these are determined independently. However, once K1 and K2 have been determined, if the two telescopes are arranged so that the radiance viewed by the two telescopes are equal, then the responsivity difference between the first and second telescopes C12 can be determined by $$C12=[S(\theta_{11})+K1*S(\theta_{12})]/[S(\theta_{21})+K2*S(\theta_{22})], \tag{12}$$

Unlike the case for the K1 and K2 determinations, determining the value of C12 does not require that the scene radiance be essentially unpolarized, only that the telescopes view the same radiance level. Thus, even if boresight misalignments exists between the paired telescopes, the averaging of a reasonable number of scene samples should reduce any residual error from this source to a negligible level.

Despite the ability to determine C12 without use of the polarization calibrator, there is one circumstance where having the same effectively unpolarized radiance viewed by each of the sensor channels would be valuable. This situation occurs when signals $S(\theta_{11})$, $S(\theta_{12})$, $S(\theta_{21})$, and $S(\theta_{22})$ can only be obtained for three of the four azimuth positions, e.g., from $S(\theta_{11})$, $S(\theta_{12})$ and $S(\theta_{21})$, in a given spectral band such as would occur if the $S(\theta_{22})$ channel were inoperable. In principle, only three components are required to determine the I, Q and U Stokes components, based on the following relationships:

$$k*S(\theta_{11})=(I+Q)/2, \tag{13}$$

$$k*K1*S(\theta_{12})=(I-Q)/2 \tag{14}$$

$$k*C12*S(\theta_{21})=(I+U)/2 \tag{15}$$

and $$k*C12*K2*S(\theta_{22})=(I-U)/2. \tag{16}$$

Also, $$I_1=k*S(\theta_{11})+k*K1*S(\theta_{12}), \tag{17}$$

$$Q=k*C12*S(\theta_{21})+k*C12*K2*S(\theta_{22}), \tag{18}$$

$$Q=k*S(\theta_{11})-k*K1*S(\theta_{21}) \tag{19}$$

and $$U=k*C12*(\theta_{21})-k*C12*K2*(\theta_2) \tag{20}$$

wherein $I_1$ represent the intensity component of the Stokes vector from the sensor channels of the first telescope. When the polarimeter has been properly calibrated, i.e., with k and C12 determined, the value of all of the Stokes parameter I, Q and U can be determined if any one of the signal values is missing. For example, if the measurement $S(\theta_{22})$ is missing, U can still be determined using the following relationship:

$$U=2*k*C12*S(\theta_{21})-k*[S(\theta_{11})+K1*S(\theta_{12})] \tag{21}$$

As can be seen by equations (13) through (21) above, therefore, it is necessary to know the correct value for C12 in order to obtain accurate results for the missing signal value. This C12 value cannot be determined using equation (12) if the measurement $S(\theta_{22})$ is missing, but must be determined using the polarization calibrator based on the following relationships for radiance samples from the polarization calibrator:

$$k*S_C(\theta_{11})=I_{C,1}/2, \tag{22}$$

$$k*C12*S_C(\theta_{21})=I_{C,2}/2, \tag{23}$$

where the subscript C denotes radiance samples from the polarization calibrator and the subscripts 1 and 2 denote radiance samples from the first and second telescope in the pair, respectively. Provided that the paired telescopes are boresighted and a specular reflector is used as the source of illumination for the polarization calibrator, the depolarized radiance samples provided by the polarization calibrator to the polarimeter will be identical. Accordingly, the correct value for C12 can be obtained from the expression $$C12=S_C(\theta_{11})/S_C(\theta_{21}). \tag{24}$$

The present invention may also include the capability to provide verification that the proper scaling factors are being used in determining the linear polarization of the scene. The need for a rescaling could be due to changes in any stress-induced birefringence in the refractive optics, cross-talk between channels measuring orthogonal polarization components, and stray light effects. This function is achieved by transmitting 100% linearly polarized light into the polarimeter, preferably based on radiance from a scene possessing the same spectral content as has been used for K1 and K2 determinations, and scaling the components of the Q and U Stokes vector components to match the calibrator polarization. More specifically, if the beam exiting the calibrator is known to be 100% linearly polarized, the ratio defined by the known polarization divided by the measured polarization is used to scale the values for the corresponding measured scene polarizations. This calculation is represented by $$Q_{SA}/I = q_{SA} = (q_{CA}/q_{CM})^* q_{SM} \quad (25)$$

from a first of the paired telescopes providing values for Q, and $$U_{SA}/I = u_{SA} = (u_{CA}/u_{CM})^* u_{SM} \quad (26)$$

from the second of the paired telescopes providing values for U, where Q represents the linear polarization component of the Stokes vector obtained from the $S(\theta_{11})$ and $S(\theta_{12})$ channels of the Q telescope and U represents the component from the $S(\theta_{21})$ and $S(\theta_{22})$ channels of the U telescope. The normalized Stokes components q, u are obtained by dividing the value of the linear polarization component by the intensity I. The subscript S denotes a radiance sample acquired by the sensor channel directly from the scene, whereas the subscript C denotes the polarized radiance sample acquired by the sensor channel from the scaling portion of the calibrator. Similarly, the subscript A indicates the actual polarization, while the subscript M indicates the measured scene Stokes component prior to any scaling corrections.

Using the relationships set forth above in equations (25) and (26), measured scene Stokes components should be corrected when the calculated $q_{CM}$ and/or $u_{CM}$ is/are significantly different from $q_{CA}$ and/or $u_{CA}$, respectively. Thus, multiplying the scaling factors, i.e., the ratios of the actual to measured Stokes components from the calibrator measurements, times the measured scene components $q_{SM}$ and $u_{SM}$, respectively, yields the actual scene Stokes components $q_{SA}$ and $u_{SA}$.

Figure 2:
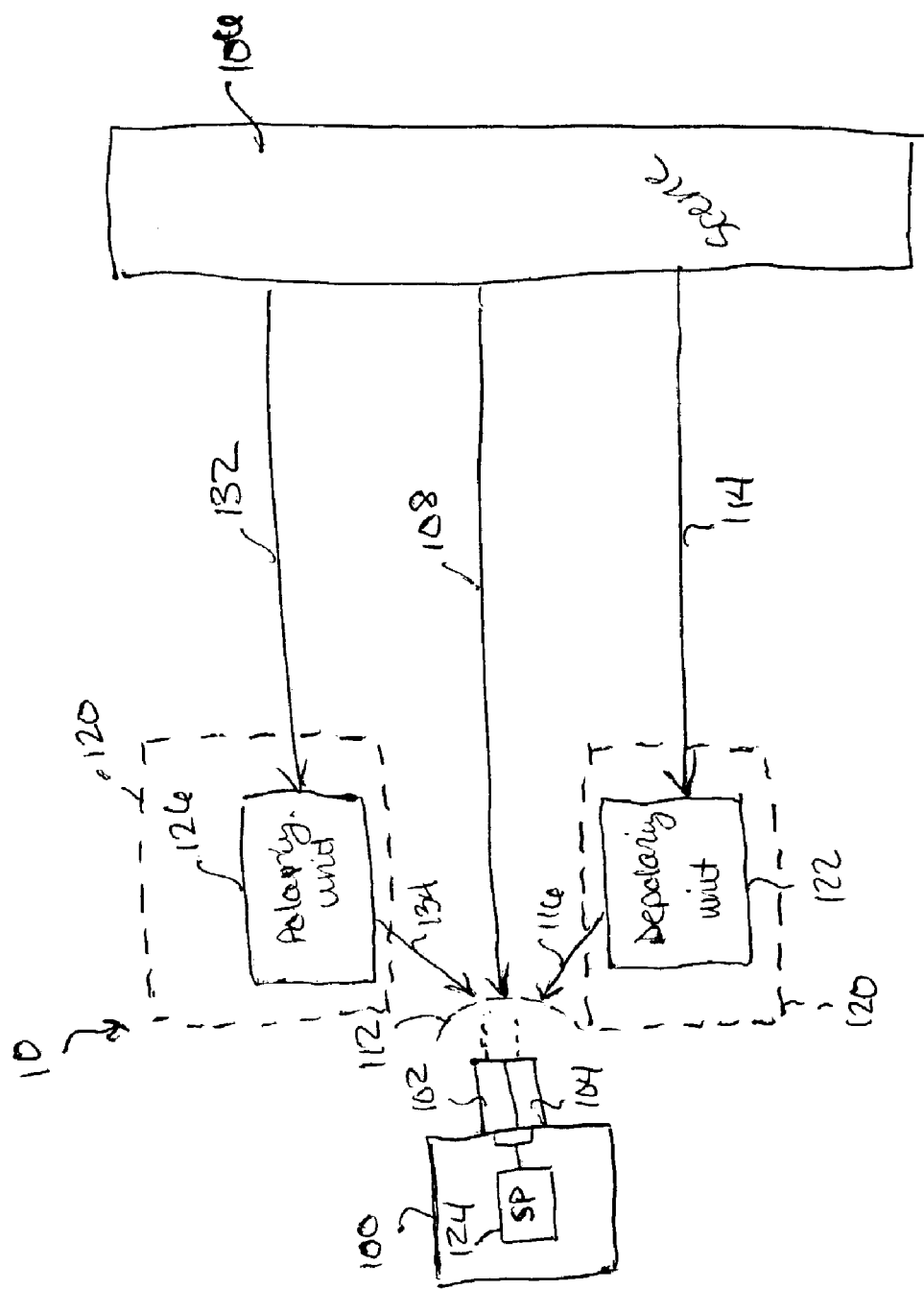
FIG. 2 is an explanatory diagram of a polarimeter and calibrator according to the present invention.

FIG. 2 generally illustrates at 10 the polarimeter 100 and calibrator 120 in accordance with the present invention. A pair of optical assemblies 102, 104 are preferably provided as a pair of parallel bore-sighted telescopes, each containing at least one sensor channel, as mentioned above. Radiance samples 108 are viewed by the telescopes 102, 104 directly from the scene 106, and are converted to signals representing the intensity and polarization measurements for each scene sample sensed by the signal processor 124 to be output with the resultant scene data from the polarimeter in the form of scene Stokes vector components.

Radiance sample 114 derived from scene 106 is substantially depolarized by the action of a polarization scrambler in the depolarization unit 122 of the calibrator 120. The unpolarized radiance sample 116 exiting the depolarization unit 122 is detected by the sensor channels within the Q and U optical assemblies (telescopes) 102, 104, whereupon the signals are routed to the signal processor 124 for analog-to-digital conversion, data formatting together with scene data, and output for storage as signals representing the detected quantities of the unpolarized sample 116. Based on the timing during the scan period and the position along the scan path at which the unpolarized sample 116 is obtained by the telescopes 102, 104, the signals outputted by the polarimeter for the unpolarized sample will be recognized as calibration data, whereupon the calibration data may be subsequently used for updating the values of K1, K2, and C12 according to equations (2) through (12) set forth above.

In this embodiment, final calculations of the scene measurement data, including processing the scene Stokes vector components with the appropriate combined Mueller matrices, and calculation of the responsivity factors and updating the calibration data of the polarimeter to yield the final accurate measurements of the scene are performed in an external processor, not shown in the figure, after completion of the measurement process. In an alternative embodiment, however, such a processor may be integrally incorporated into the polarimeter and calibrator system as one complete unit to directly receive the output from the signal processor 124 or the sensor channels and perform the necessary data reduction calculations.

Figure 3:
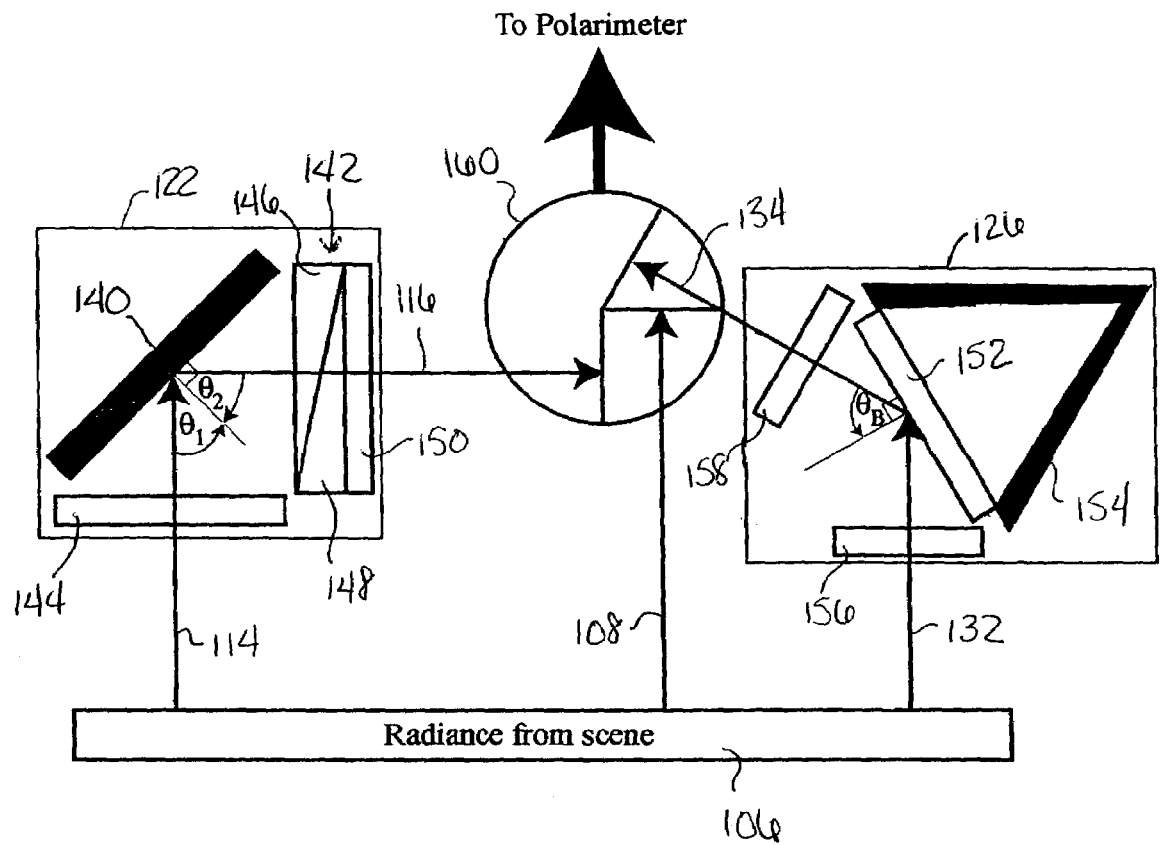
FIG. 3 is a more detailed illustration of the operative features of the calibrator and polarimeter which acquire radiance samples from the scene.

The optional polarization unit 126 of the calibrator 120 is also shown in FIG. 3. Radiance sample 132 is received in the polarization unit 126 and converted to a radiance sample which is essentially 100% linearly polarized 134, which is then viewed by the telescopes 102, 104. The sensor channels in telescopes 102, 104 detect the polarized inputs such that suitable scaling factors can be determined from the data provided from the polarimeter. As with the measurement data for the unpolarized sample, the measurement data for the polarized sample will be recognized as data to be used for scaling the polarization magnitudes of the radiance samples directly obtained from the scene, based on the timing during the scan period and the position along the scan path at which the polarized sample is obtained by the polarimeter. The measurement data for the polarized sample may then by subsequently used to properly scale the polarization magnitudes of the scene measurement data for the directly viewed radiance samples, according to the relationships set forth in equations (25) and (26) above.

The depolarization unit 122 and the polarization unit 126, if applicable, are located in proximity to the polarimeter 100 such that the unpolarized sample 116 and the polarized sample 134 output by the depolarization unit 122 and the polarization unit 126, respectively, can be detected during the scanned path 112 during each scan cycle. Preferably, the units 122, 126 are located at the peripheries of path 112 so that the depolarized sample 116 and the polarized sample 134 are detected before and after the radiance samples 108 are obtained directly from the scene, as seen in FIG. 2. Moreover, the signal processor 124 of the polarimeter 100, the depolarization unit 122 and optionally the polarization unit 126 of the calibrator 120 are provided in one unitary housing, or may be provided in separable housings mounted together and operatively connected.

FIG. 3 is a more detailed illustration of the structural components of the depolarization unit 122 and the polarization unit 126 of the calibrator 120, and also of an optional selector 160 provided in the polarimeter 100.

Depolarization unit 122 includes a reflector 140, a polarization scrambler 142, and an optional protective window 144. The reflector 140 may be chosen to be either a diffuse or a specular reflector. The preferred embodiment of the invention uses a specular reflector, such as a high reflectance mirror, because a specular reflector offers better control of the radiance uniformity for the relative responsivity determination than can be achieved using a diffuse reflector. This is important in order to obtain the most accurate determination of the factor C12 as discussed above. With a diffuse reflector, the obtained radiance level of a sample is dependent on the angular subtense of the scene providing the illumination, and therefore tends to vary between the different areas viewed by the paired telescopes. The angle of incidence $\theta_1$ on the reflector 140 is not critical, and can be selected based on design considerations apart from the calibration aspects of the invention. (Note that for specular reflection, $\theta_1 = \theta_2$)

Figure 4:
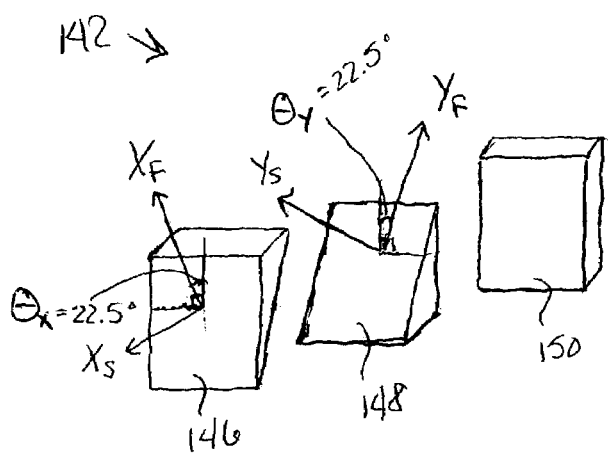
FIG. 4 is an explanatory illustration of the scrambler assembly in the depolarization unit of the calibrator.

Preferably, the polarization scrambler 142 includes two wedge prisms 146, 148 formed of a birefringent material, e.g., crystalline quartz, with the fast and slow axes of each prism being parallel to the plane-parallel outer faces of the polarization scrambler assembly and with the fast axes $X_F$, $Y_F$ of the two wedge prisms oriented at 45° in azimuth to each other and at approximately 22.5° (or 67.5°) to the wedge direction (FIG. 4). To minimize any polarization introduced into beam 116 upon exiting the wedge prisms 146, 148 of the scrambler 142, an isotropic plane-parallel plate 150 can be added to the exit side of the scrambler. The plate material is chosen so that its refractive index (in all directions) approximately equals the average of the spectral refractive indices of the fast and slow directions ($X_F$, $Y_F$, $X_S$, $Y_S$) of the prism material. Finally, to minimize internal reflections, the three elements of the polarization scrambler 142 are joined either by optically contacting or adhesively bonding the elements together (with a material of comparable refractive index).

The placement of a protective window 144 in the depolarization unit 122 as shown in FIG. 2 is optional, but is useful since this reduces the number of exposed surfaces in the depolarization unit 122 from three to two and localizes the likely surface contamination to exterior surfaces which simplifies cleaning, should this be necessary.

The polarization unit 126 includes a polished, plane-parallel dielectric plate 152 preferably made of a relatively high refractive index isotropic glass, a trap cavity 154, and two protective windows 156 and 158. The glass plate 152 is used to view the scene radiance 132 from the scene 106 at the Brewster angle, i.e., $\theta_B = \arctan(n)$ where n is the refractive index of the plate 152. If viewed precisely at the Brewster angle, the reflected beam 134 will be 100% linearly polarized. Light trap 154 serves to provide an essentially zero radiance background for the complementary transmitted beam that is superimposed onto the beam directly reflected from the scene towards the polarimeter from the Brewster plate 152. Preferably, light trap 154 is formed as angled black or dark surfaces oriented so that when viewed through the glass plate 152 at the Brewster angle, any scene radiance transmitted through the Brewster plate is trapped so as to avoid any significant portion being redirected and superimposed onto the Brewster plate calibration (reflected) beam.

Since contamination of the plate 152 can affect both the reflectance and polarization of the reflected radiance beam 134, it is important to provide protective windows 156, 158 at both the light input and output sides of the polarization unit 126. Although it is acceptable to position both of these windows at a 90° angle of incidence to the respective directions of radiance beam 132 and the reflected radiance sample beam 134 to provide the most compact arrangement of the polarization unit 126, it is preferable to orient the window 158 on the polarimeter side at the Brewster angle for maximum transmission of the polarized beam 134.

Selector 160 is preferably embodied as a continuously-rotating, polarization-compensated scanner which selectively transmits the unpolarized radiance samples 116, the direct scene radiance samples 108, and the polarized radiance samples 134 to the sensor channels contained in the telescopes 102, 104 of the polarimeter, ideally without modifying the polarization state of any of the inputs. Preferably, selector 160 includes a system of mirrored surfaces enclosed by protective windows, in which the mirrored surfaces are arranged to reflect the selected radiance sample to the polarimeter without changing the polarization of the radiance samples. Furthermore, the depolarization unit 122 and the selector 160 are preferably mutually positioned so that the selector 160 captures the unpolarized beam 116 at the location at which the beam 116 exits at an angle normal to the exterior surface of the polarization scrambler 142, since the beam 116 is most effectively unpolarized with this geometry. It is noted that in FIG. 3, selector 160 is shown only as a schematic representation of its functional capability, and not necessarily as a depiction of the disclosed structural arrangement thereof.

During a sampling operation according to the present invention, the scanner continuously rotates while the sensor channels in the paired telescopes obtain radiance samples at a predetermined increment, e.g., every 0.8° of scanner rotation. For purposes of further explanation, assume the scanner rotates counterclockwise as viewed in FIG. 3 and that the scan path begins with the leading edge of depolarization unit 122 in view. As the selector rotates past the depolarization unit 122, the polarimeter obtains a number of unpolarized radiance samples 116 which may be used to calibrate the polarimeter as described above using equations (2) through (12). The scanner then rotates across the scene, to thereby direct a plurality of direct scene radiance samples 108 to the polarimeter. If a polarization unit 126 is provided, the scanner then rotates towards and past the polarization unit, whereupon the polarimeter obtains a number of polarized samples while viewing the polarization unit. As the selector 160 rotates beyond the polarization unit 126 (or scene 106 if polarization unit 126 is not provided), the polarimeter will view a dark reference zone until the selector again rotates towards the depolarization unit 122. Allowing the polarimeter to view the dark reference zone during each scan cycle permits periodic dc-restoration of the sensor channels to preserve dynamic range and collect of "dark signal" samples for accurate signal offset corrections. Since unpolarized samples, scene radiance samples and polarized samples are obtained during each scanning cycle, use of the selector 160 thus provides the advantage of enabling the polarimeter to obtain unpolarized radiance samples 116 (for calibrating the relative responsivities of the telescopes), polarized radiance samples 134 (for scaling the polarization magnitude in the scene measurement data) and direct scene radiance samples 108 (for producing scene measurement data), all interspersed within each scan.

It is noted that substantially the same effect provided by the depolarization unit 122 can be provided by simply interposing a polarization scrambler in between the scene and the polarimeter when the polarimeter is oriented to obtain direct scene radiance views, e.g., radiance sample 108 in FIG. 3. The present invention, however, provides the advantage of fixedly locating depolarization unit 122 with respect to the polarimeter, which thereby enables many more calibration procedures to be performed than would be feasible under the relatively infrequent calibrations described here. Moreover, use of the selector 160 automatically and continuously enables calibration data to be interspersed with the scene measurement data to thereby provide more effective calibration of the polarimeter at the time any changes in conditions occur. As a part of the calibration process, it is desirable that a polarization scrambler be occasionally placed in the path of the direct scene radiance sample 108 for comparison purposes with the calibration results obtained with the depolarization unit 122 of the calibrator.

In the method according to the present invention, the polarimeter and calibrator system described above can be used to obtain updated calibration information of the polarimeter during operation of the polarimeter to collect scene radiance samples until all the desired scene samples have been acquired. Further explanation of the method will now be provided with reference to FIGS. 5A–5C and 6A–6B.

Figure 5A:
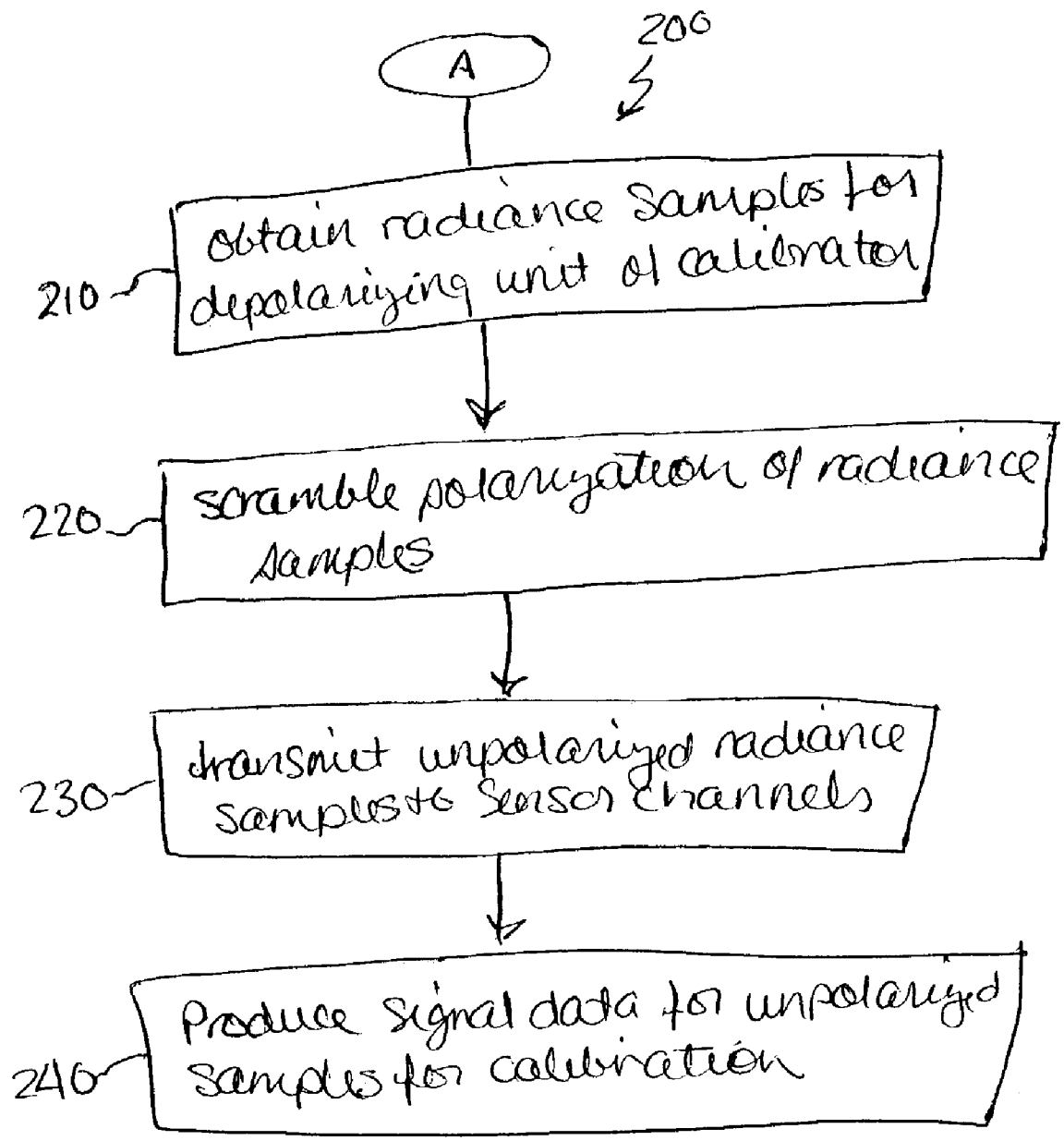
FIG. 5A is a flowchart for generally representing the procedure for calibrating the polarimeter.
Figure 5B:
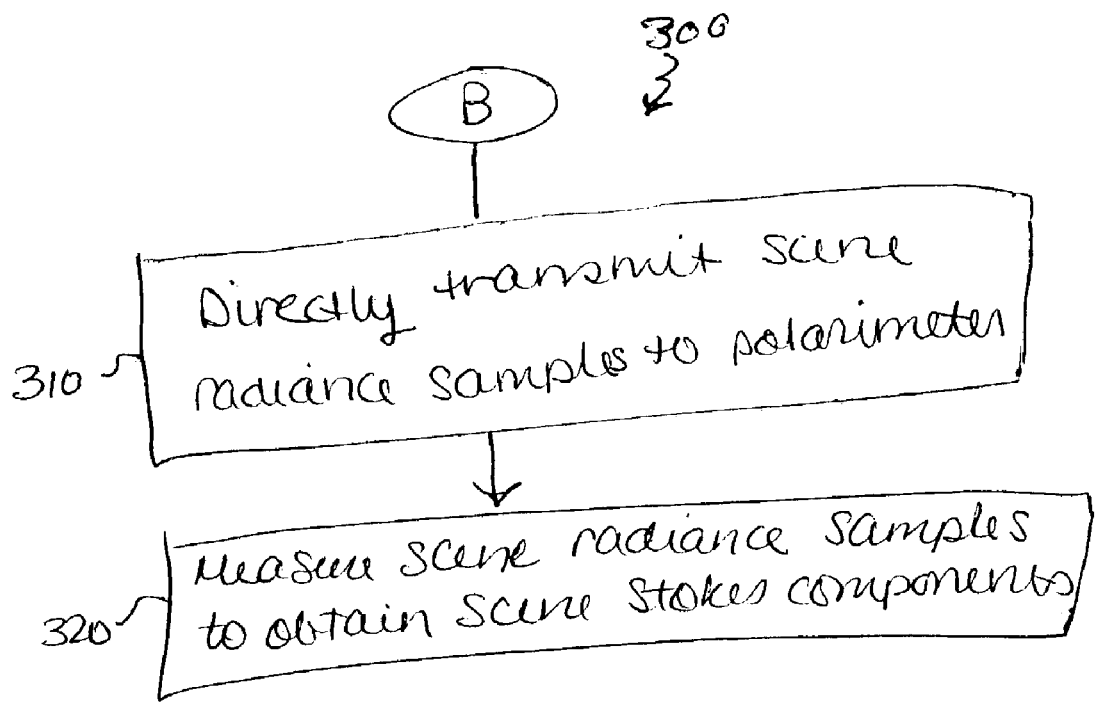
FIG. 5B is a flowchart for generally representing the procedure for directly sampling scene radiance samples for obtaining scene measurement data.

As shown in FIG. 5A, the calibration procedure 200 includes receiving at least one radiance sample in the a depolarizing unit of the calibrator 210, polarization scrambling the at least one radiance sample received in the depolarizing unit 220, transmitting the scrambled radiance sample(s) to be viewed by the paired telescopes of the polarimeter for detection by the sensor channels therein 230, and producing unpolarized signal data by the polarimeter to be used for calculating the intra- and inter-telescope responsivity factors using equations (2) through (12) set forth above 240. As shown in FIG. 5B, the scene sampling procedure 300 includes directly collecting at least one radiance sample from a scene viewed by the paired telescopes in the polarimeter 310, and producing intensity and polarization data for each scene radiance sample 320. The procedures 200, 300 are preferably performed for each of a plurality of scanning cycles, so that the unpolarized calibration data is obtained along with the direct scene radiance data during each scan cycle.

As mentioned above, the system and method of the present invention is especially useful for polarimetric applications performed over a large geographical area with the polarimeter and calibrator mounted and operating on a platform which is in constant motion, such as on an aircraft. According to the method of the invention, therefore, after the calibration procedure and the scene sampling procedure have been performed through one complete scanning cycle, the platform has also been moved to a different location of the scene, and the calibration procedure and scene measurement procedure are again performed during another scanning cycle at the new location. These procedures can be repeated continuously for any number of scanning cycles until scene samples have been obtained for the entire scene of interest.

By enabling calibration data to be collected throughout the operation of collecting scene data, the present invention advantageously enables the calibration data for the polarimeter to be updated to reflect changes due to time, temperature, contamination, pressure, etc. as each change occurs. It should be realized, however, that the integrated system and method of the present invention is not restricted for use in mobile applications as described above. To the contrary, the present invention is suitable for any field of use and in any environment, including in traditional applications, in indoor settings, and with a stationary instrument platform and stationary subject matter being viewed through the polarimeter.

Transmission of the scene radiance samples directly to the paired telescopes of the polarimeter and transmission of the unpolarized radiance samples from the depolarizing unit to the paired telescopes may be performed by manually directing the paired telescopes to view the output of the depolarizing unit of the calibrator and resultant sample(s), and then orienting the paired telescopes to directly view the scene to obtain the scene radiance samples. Of course, using this method, it is not required that each procedure be performed in any particular order or with any particular frequency. Instead, the calibration procedure may be performed at lesser intervals as warranted by changes in conditions that justify an update of the calibration data.

Figure 6A:
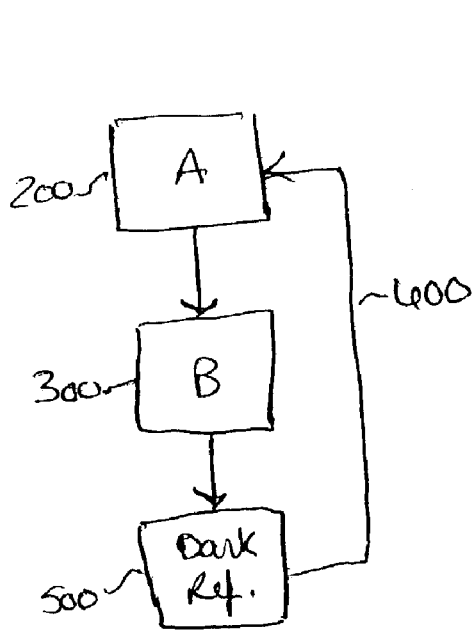
FIG. 6A is a flowchart for illustrating one embodiment of the method according to the present invention.

Another method for transmitting the unpolarized samples and the scene radiance samples to the paired telescopes entails automatically transmitting the samples using a switching mechanism such as a rotating selector which automatically and periodically directs the radiance samples from the depolarization unit and the scene, respectively, to the paired telescopes. In this method using a rotating selector, the paired telescopes are also allowed to view a dark reference zone for a portion of the selector rotation cycle. As discussed above, allowing the polarimeter to view the dark reference zone during each scan cycle permits periodic dc-restoration of the sensor channels in the paired telescopes to preserve dynamic range and collection of "dark signal" samples for signal offset corrections. This method is illustrated in FIG. 6A, in which the procedure 200 for obtaining unpolarized signal data for calibrating the polarimeter to reflect any changes in relative responsivities of the two telescopes is performed, then the procedure 300 for obtaining scene measurement data for the direct scene radiance samples is performed, next the procedure 500 for allowing the polarimeter to view a dark reference zone is performed, and finally these sequences are repeated in an endless loop 600 until the entire scene of interest has been sampled. Of course, this method of the present invention is not restricted to performing procedures 200, 300 and 500 in the order described above and shown in FIG. 6A. For example, the invention encompasses variations of this method in which the procedures 200, 300 and 500 are performed in a sequence other than that described herein, such as may be achieved with a selector having a different signal transmission profile and/or movement pattern, and a variation in which procedure 500 is omitted so that only prodedures 200 and 300 are performed alternately and repeatedly.

Calculation of the calibration data, specifically the relative intra-and inter-telescope responsivity factors and processing the scene measurement data with the combined Mueller matrices and with the updated calibration data are, in one embodiment of the invention, performed subsequent to the operation of collecting scene radiance samples for the entire scene of interest. In this case, the signal data providing the Stokes vector quantities from the unpolarized and directly obtained radiance samples in the polarimeter are stored during operation of the polarimeter, and subsequently used for calculation and analysis. In another embodiment, the calculation of the calibration data and the Mueller matrix processing are performed in a processor integrally provided with the operationally integrated polarimeter and calibrator system or the calibrator according to the invention.

Figure 6B:
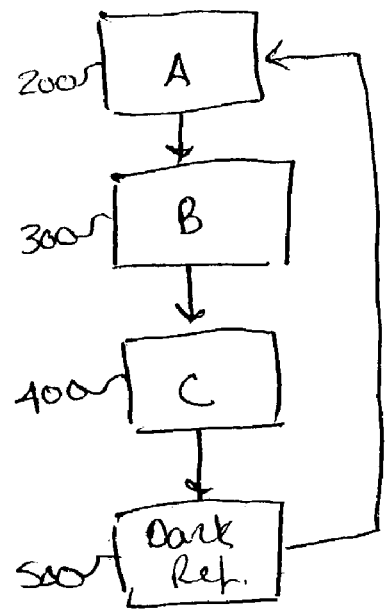
FIG. 6B is a flowchart for illustrating another embodiment of the method according to the present invention.
Figure 5C:
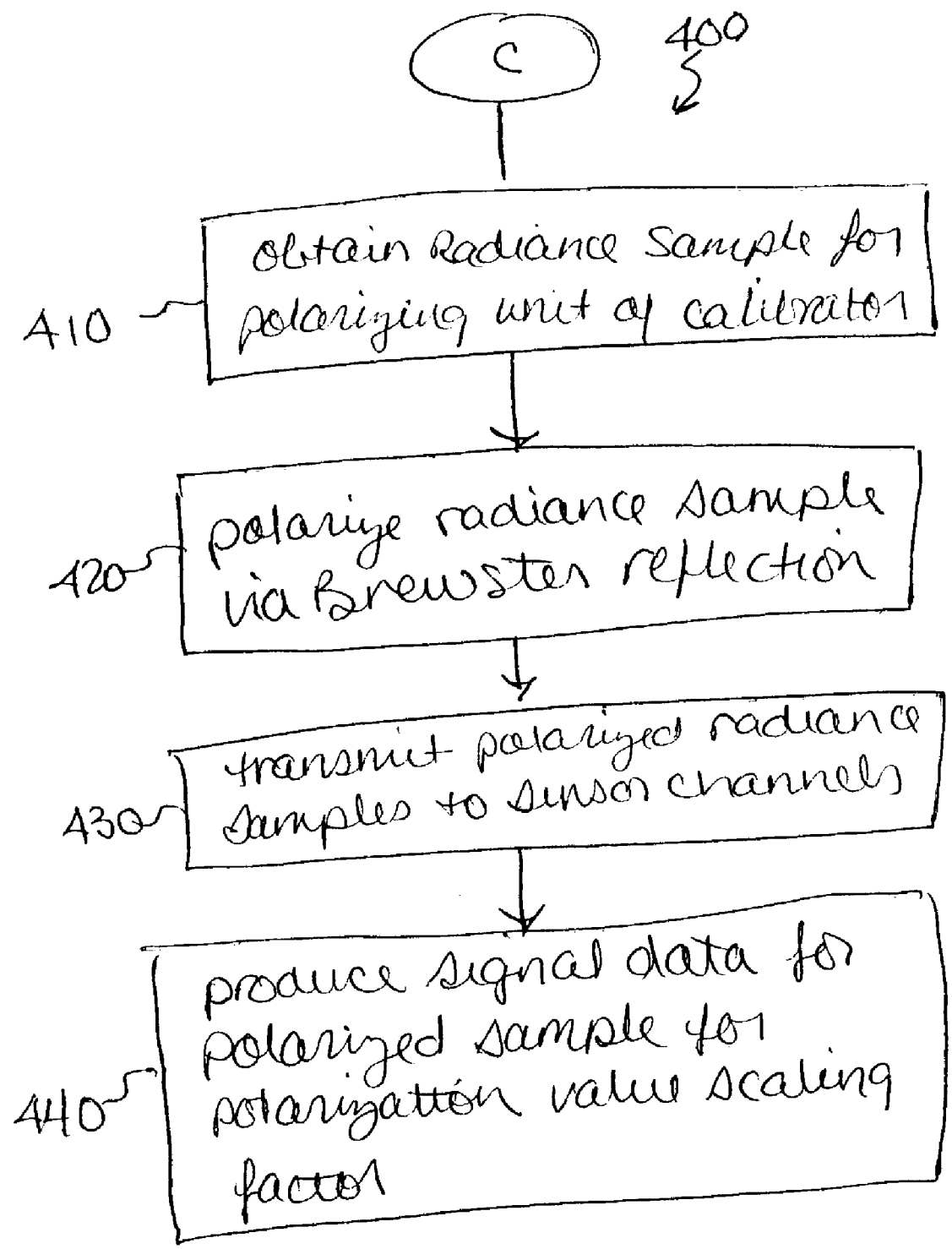
FIG. 5C is a flowchart for generally representing the procedure for scaling the polarization values of the measured scene data output from the polarimeter.

The method of the present invention may further include a procedure 400 for scaling the magnitude of the output values representing the measured polarization of the scene. This procedure, illustrated in FIG. 5C, includes obtaining at least one radiance sample of the scene in a polarizing unit of the calibrator 410, polarizing the at least one radiance sample received in the polarizing unit to be substantially 100% linearly polarized 420, transmitting the at least one polarized radiance sample to the sensor channels in the Q and U telescopes of the polarimeter 430, and producing signal data for the polarized samples processed by the polarimeter for correcting the polarization magnitude of the direct scene measurements using the relationships set forth in equations (25) and (26) above 440. Preferably, this scale factor calibration procedure 400 is also performed in continuously alternating fashion as illustrated in FIG. 6B along with the responsivity calibration procedure 200, the scene sampling procedure 300, and the dark reference zone viewing procedure 500. As described above, the alternating procedures may be performed by cyclically orienting the paired telescopes to directly view the output of the depolarizing unit of the calibrator to obtain the polarization-scrambled scene radiance measurements, toward the scene to obtain direct scene radiance measurements, and toward the polarizing unit of the calibrator to obtain the linearly polarized radiance measurements, or these may be performed automatically using the selector 160 shown in FIG. 3. As with the embodiment shown and described with reference to FIG. 6A, this method of the present invention is not limited to the specific arrangement shown in FIG. 6B, since the present invention also encompasses variations of this method including those in which the procedures 200, 300, 400 and 500 are performed in a different order than that explicitly disclosed herein, and those variations in which procedure 500 is omitted.

As with the calibration calculations, in one embodiment, the signal data for the polarized samples output by the polarimeter for calculating scaling factors representing the level of polarization in the measured scene data may be stored until after the scene sample collection operation, and then the calculations are performed in an external processor. In another embodiment, the polarization magnitude scaling factors are calculated in a processor integrally provided with the polarimeter and/or the calibrator, and the magnitude of the measured scene data is updated accordingly.

The processes and systems described above illustrate preferred methods and representative systems of which many variations and modifications thereof could be used and produced. The above description and drawings illustrate embodiments, which achieve the objects, features, and advantages of the present invention. However, it is not intended that the present invention be strictly limited to the above-described and illustrated embodiments. Any modifications, though presently unforeseeable, of the present invention that comes within the spirit and scope of the following claims should be considered part of the present invention.

What is claimed as new and desired to be protected by Letters Patent of the United States is:

1. An integrated polarimetric imaging system, comprising:
   a polarimeter including a pair of optical assemblies each having at least one sensor channel which receives radiance samples from a scene and outputs scene measurement data from the received radiance samples; and
   a calibrator operationally integrated with the polarimeter, the calibrator including a depolarization unit which receives radiance samples from the scene, substantially depolarizes the radiance samples received from the scene and transmits the depolarized radiance samples to be received by the polarimeter,
   wherein measurement data outputted by the polarimeter upon receiving the substantially depolarized radiance samples constitute calibration data to be used for calibrating the polarimeter.

2. The integrated system according to claim 1, wherein the measurement data outputted by the polarimeter upon receiving the substantially depolarized radiance samples includes calibration data to be used for calibrating relative responsivity factors of each optical assembly and between the pair of optical assemblies for sensing the Q and U Stokes vector components.

3. The integrated system according to claim 1, wherein the calibrator further includes a processing unit which calculates calibration data for the each of the optical assemblies based on the depolarized radiance sample and which updates measurement data from the polarimeter based on the calculated calibration data.

4. The integrated system according to claim 1, wherein the depolarization unit includes a polarization scrambler assembly which includes two wedge prisms each comprised of a birefringent material, and an isotropic plate.

5. The integrated system according to claim 4, wherein in the depolarization unit, each wedge prism comprises:
   a vertical face, an angled face opposing the vertical face, and a wedge direction defined by the vertical and angled faces;
   a fast axis defined in a direction which is parallel to an external surface of the scrambler assembly and at an angle of approximately 22.5° to the wedge direction;
   a slow axis defined orthogonally to the direction of the fast axis and parallel to the external surface of the scrambler; and
   different refractive indices in the fast and slow axis directions,
   wherein the two wedge prisms are arranged such that the angled faces of the wedge prisms are in contact with each other and the fast axes of the wedge prisms are oriented at an approximately 45° angle from each other, and
the isotropic plate comprises:
   opposing faces which are plane parallel, and
   an isotropic refractive index approximately equal to the average of the refractive indices of the fast and slow directions of the wedge prisms,
   wherein the isotropic plate is placed in contact with the vertical face of one of the wedge prisms at the side of the two wedge prisms through which a radiance sample received in the depolarization unit exits the scrambler assembly.

6. The integrated system according to claim 4, wherein the depolarization unit further includes a reflector which receives the scene radiance samples and directs them through the scrambler assembly.

7. The integrated system according to claim 6, wherein the reflector is a specular reflector.

8. The integrated system according to claim 6, further comprising a protective window through which the radiance sample enters the depolarization unit.

9. The integrated system according to claim 1, further comprising a selector which automatically and cyclically transmits scene radiance samples directly from the scene to the pair of optical assemblies, and the substantially depolarized radiance samples from the depolarization unit to the pair of optical assemblies.

10. The integrated system according to claim 1, further comprising a polarization unit which receives radiance samples from the scene, transforms the received radiance samples into essentially 100% linearly polarized samples, and transmits the polarized samples to the polarimeter, and wherein the measurement data outputted by the polarimeter upon receiving the polarized samples includes data to be used for calculating polarization scaling factors representing corrections that may be indicated to the Q and U Stokes vector components of the scene.

11. The integrated system according to claim 10, wherein the polarization unit includes
   an optically polished dielectric plate having a high refractive index and arranged so that the radiance sample received in the polarization unit is incident upon the plate at the Brewster angle and becomes essentially 100% polarized upon being reflected from the plate; and
   a light trap provided behind the plate relative to the direction from which the radiance sample is received at the plate, the light trap being formed so that any radiance flux from the scene radiance sample transmitted through the plate is trapped so as to avoid any significant portion of the radiance flux is trapped so as to avoid a significant portion being redirected and superimposed onto the plate.

12. The integrated assembly according to claim 11, wherein the polarization unit further includes first and second protective windows arranged so that the radiance sample passes through the first protective window before striking the plate and so that the polarized sample passes through the second protective window upon exiting the polarization unit.

13. The integrated assembly according to claim 12, wherein the first protective window is arranged at an angle normal to the direction at which the radiance sample enters the polarization unit and the second protective window is arranged at an angle normal to the direction at which the polarized sample exits the polarization unit.

14. The integrated assembly according to claim 12, wherein the first protective window is arranged at an angle normal to the direction at which the radiance sample enters the polarization unit and the second protective window is arranged at the Brewster angle to the direction at which the polarized sample exits the polarization unit.

15. The integrated system according to claim 10, further comprising a selector for automatically and alternately transmitting a scene radiance sample directly from the scene to the polarimeter, the substantially depolarized radiance sample from the depolarization unit to the polarimeter, and the polarized sample from the polarization unit to the at least one sensor channel, the selector capable of transmitting the samples without changing the polarization state of any of the scene radiance sample, the substantially depolarized radiance sample, and the polarized sample.

16. The integrated system according to claim 10, wherein the calibrator further includes a processing unit which calculates calibration data for the each of the optical assemblies based on the depolarized radiance sample, which calculates a scaling factor representing a magnitude of polarization of the scene measurement data, and which updates the scene measurement data based on the calculated calibration data and the calculated scaling factor.

17. An apparatus for calibrating a polarimeter, comprising:
   a depolarization unit including
      a reflector for receiving radiance samples from a scene, and
      a polarization scrambler assembly for substantially depolarizing the radiance samples received from the scene and transmits the depolarized radiance samples to be detected by the polarimeter for generating calibration data based on the depolarized radiance samples for calibrating the polarimeter, wherein the depolarization unit is adapted to be operationally integrated with the polarimeter.

18. The apparatus according to claim 17, wherein the polarization scrambler assembly includes two wedge prisms each made of a birefringent material, and an isotropic plate.

19. The apparatus according to claim 18, wherein each wedge prism comprises:
   a vertical face, an angled face opposing the vertical face, a wedge direction defined by the vertical and angled faces;
   a fast axis defined in a direction which is parallel to an external surface of the scrambler assembly and at an angle of approximately 22.5° to the wedge direction;
   a slow axis defined orthogonally to the direction of the fast axis and parallel to the external surface of the scrambler assembly; and
   different refractive indices in the fast and slow axis directions,
   wherein each wedge prism is formed of a birefringent material, and
   wherein the two wedge prisms are arranged such that the angled faces of the wedge prisms are in contact with each other and the fast axes of the wedge prisms are oriented at an approximately 45° angle from each other, and
wherein the isotropic plate comprises:
   opposing faces which are plane parallel, and
   an isotropic refractive index approximately equal to the average of the refractive indices of the fast and slow directions of the wedge prisms,
   wherein the isotropic plate is placed in contact with the vertical face of one of the wedge prisms at the side of the two wedge prisms through which a radiance sample received in the depolarization unit exits the scrambler assembly.

20. The apparatus according to claim 17, wherein the reflector is a specular reflector.

21. The apparatus according to claim 17, further comprising a protective window through which the radiance sample enters the depolarization unit.

22. The apparatus according to claim 17, wherein the depolarizer is used for obtaining relative responsivity data for the polarimeter.

23. The apparatus according to claim 17, further comprising a polarization unit which receives a radiance sample from the scene, transforms it into a essentially 100% linearly polarized sample, and transmits the polarized sample to be detected by the polarimeter for generating data to be used for calculating factors for correcting polarization of scene data measured by the polarimeter.

24. The apparatus according to claim 23, wherein the polarization unit includes
   a polished dielectric plate having a refractive index is arranged so that the radiance sample received in the polarization unit is incident upon the plate at the Brewster angle and becomes essentially 100% linearly polarized upon being reflected from the plate; and
   a light trap provided behind the plate relative to the direction from which the radiance sample is received at the plate, the light trap being formed so that any radiance flux from the scene radiance sample transmitted through the plate is trapped so as to avoid any significant portion of the radiance flux is trapped so as to avoid a significant portion being redirected and superimposed onto the plate.

25. The apparatus according to claim 24, wherein the polarization unit further includes first and second protective windows arranged so that the radiance sample passes through the first protective window before striking the plate and so that the polarized sample passes through the second protective window upon exiting the polarization unit.

26. The apparatus according to claim 25, wherein the first protective window is arranged at a normal angle to the direction at which the radiance sample enters the polarization unit and the second protective window is arranged at a normal angle to the direction at which the polarized sample exits the polarization unit.

27. The apparatus according to claim 25, wherein the first protective window is arranged at a normal angle to the direction at which the radiance sample enters the polarization unit and the second protective window is arranged at the Brewster angle to the direction at which the polarized sample exits the polarization unit.

28. A calibrator adapted to be integrally assembled with a polarimeter for use during operation of the polarimeter, comprising:
  a depolarization unit which receives a radiance sample from a scene, substantially depolarizes the radiance sample received from the scene and transmits the depolarized radiance sample to at least one sensor in a polarimeter; and
  a processing unit which receives at least two input intensity signals from each sensor in the polarimeter, the input intensity signal being based on the depolarized radiance sample transmitted to the at least one sensor, wherein the processing unit calculates at least one responsivity factor for the at least one sensor and transmits the calculated at least one responsivity factor to a processing unit in the polarimeter.

29. A method of calibrating a polarimeter during operation of the polarimeter, comprising:
  a) receiving at least one radiance sample from a scene in a depolarization unit;
  b) substantially depolarizing the at least one radiance sample;
  c) outputting the at least one substantially depolarized radiance sample from the depolarization unit to be transmitted to at least one optical assembly in a polarimeter;
  d) receiving the at least one substantially depolarized radiance sample in the at least one optical assembly;
  e) outputting signal data from the polarimeter based on the at least one substantially depolarized radiance sample to be used for calibrating the at least one optical assembly;
  f) directly obtaining at least one radiance sample from the scene in the at least one optical assembly;
  g) outputting scene measurement data based on the at least on directly obtained radiance sample; and
  h) repeating acts a) through g) for each of a plurality of sets of radiance samples of the scene.

30. The method according to claim 29, wherein the at least one depolarized sample and the at least one directly obtained radiance sample are received by the at least one optical assembly by orienting the at least one optical assembly so that it is directed at the depolarization unit to thereby receive the at least one outputted depolarized sample, and orienting the at least one optical assembly so that it is aligned directly with the scene to thereby receive the at least one directly obtained radiance sample.

31. The method according to claim 29, wherein the at least one depolarized sample and the at least one directly obtained radiance sample are received by the at least one optical assembly automatically by a selector which cyclically receives and directs the at least one depolarized radiance sample outputted by the depolarization unit toward the at least one optical assembly, and receives and directs the at least one radiance sample directly from the scene toward the at least one optical assembly.

32. The method according to claim 31, further comprising:
  i) transmitting a dark reference zone to be viewed by the at least one optical assembly; and
  wherein h) includes repeating acts a) through g) and i) for each of a plurality of sets of radiance samples of the scene.

33. The method according to claim 31, further comprising:
  i) calculating relative responsivity factors of the at least one optical assembly based on the signal data outputted in e).

34. The method according to claim 29, wherein the acts a) through h) are performed on a moving platform.

35. The method according to claim 29, wherein the signal data outputted from the polarimeter based on the at least one substantially depolarized radiance sample is to be used for calculating a relative responsivity factor for each of the at least one optical assembly.

36. The method according to claim 29, further comprising:
  i) receiving a radiance sample from the scene in a polarization unit;
  j) transforming the radiance sample received in i) into an essentially 100% linearly polarized sample;
  k) outputting the polarized sample from the polarization unit to be transmitted to at least one optical assembly;
  l) receiving the at least one polarized sample in the at least one optical assembly; and
  m) outputting signal data from the polarimeter based on the at least one polarized sample to be used for calculating a scaling factor for the magnitude of linear polarization in the scene measurement data obtained in g); and
  wherein h) includes repeating acts a) through g) and i) through m) for each of a plurality of sets of radiance samples of the scene.

37. The method according to claim 36, wherein each of the at least one radiance sample received in i) is respectively transformed into an essentially 100% linearly polarized sample by reflecting each of the at least one radiance sample on a smooth dielectric surface at the Brewster angle.

38. The method according to claim 36, wherein the at least one depolarized sample, the at least one directly obtained radiance sample and the at least one polarized sample are received by the at least one optical assembly by orienting the at least one optical assembly so that it is directed at the depolarization unit to thereby receive the at least one outputted depolarized sample, orienting the at least one optical assembly so that it is aligned directly with the scene to thereby receive the at least one directly obtained radiance sample, and orienting the at least one sensor channel so that it is directed at the polarization unit to thereby receive the at least one outputted polarized sample.

39. The method according to claim 36, wherein the at least one depolarized sample, the at least one directly obtained radiance sample and the at least one polarized sample are received by the at least one sensor channel automatically by a selector which cyclically receives and directs the at least one depolarized radiance sample outputted by the depolarization unit toward the at least one optical assembly, receives and directs at least one radiance sample directly from the scene toward the at least one optical assembly, and receives and directs the at least one polarized sample outputted by the polarization unit toward the at least one optical assembly.

40. The method according to claim 39, further comprising:
  n) transmitting a dark reference zone to be viewed by the at least one optical assembly; and
  wherein h) includes repeating acts a) through g) and i) through n) for each of a plurality of sets of radiance samples of the scene.

41. The method according to claim 36, further comprising:
  n) calculating a scaling factor for the magnitude of linear polarization in the scene measurement data obtained in g) based on the signal data outputted in m).

42. The method according to claim 36, wherein the acts a) through m) are performed on a moving platform.

* * * * *